United States Patent [19]

Juda et al.

[11] Patent Number: 4,693,894
[45] Date of Patent: Sep. 15, 1987

[54] HALOPHOR COMPOSITION

[75] Inventors: Robert H. Juda, Akron; Roger A. Crawford, Wadsworth, both of Ohio; Paritosh M. Chakrabarti, Pittsburgh, Pa.

[73] Assignee: PPG Industries, Inc., Pittsburgh, Pa.

[21] Appl. No.: 819,440

[22] Filed: Jan. 16, 1986

[51] Int. Cl.$^4$ ............................................. A61K 33/18
[52] U.S. Cl. .................................................. 424/150
[58] Field of Search ................................. 424/150, 78

[56] References Cited

U.S. PATENT DOCUMENTS

| 2,759,869 | 8/1956 | Sutton et al. | 167/70 |
|---|---|---|---|
| 2,868,686 | 1/1959 | Shelanski et al. | 167/17 |
| 3,067,089 | 12/1962 | Winslow | 167/17 |
| 3,277,010 | 10/1966 | Schenck et al. | 252/106 |
| 4,444,756 | 4/1984 | Schlüssler et al. | 424/150 |
| 4,526,751 | 7/1985 | Gartner | 424/150 X |

FOREIGN PATENT DOCUMENTS 1252774 10/1971 United Kingdom .
1355359 5/1974 United Kingdom .

*Primary Examiner*—Leonard Schenkman
*Attorney, Agent, or Firm*—Irwin M. Stein

[57] ABSTRACT

Complexes of bromine and/or iodine, the dihalide of poly(ethylene glycol) and alkali metal or alkaline earth metal halide are described. In particular, complexes of bromine with poly(ethylene glycol) dichloride and alkali metal halide, e.g., lithium or sodium bromide, are described.

34 Claims, No Drawings

HALOPHOR COMPOSITION

DESCRIPTION OF THE INVENTION

The present invention relates to biocidal bromine- and iodine-containing compositions and, in particular, relates to complexes of bromine and/or iodine with dihalides, e.g., dichlorides, dibromides or difluorides of poly(ethylene glycols). More particularly, the present invention relates to solid, free-flowing biocide compositions of particulate amorphous siliceous carrier having the aforesaid complex adsorbed thereon.

The halogens, i.e., chlorine, bromine and iodine, are recognized as excellent biocidal materials and are used extensively, particularly in the food processing and handling industries, to prevent bacteriological contamination of foodstuffs. Halogen sanitizers are also used in controlling potentially harmful organisms in potable water, swimming pools, hospitals, and wherever harmful organisms can present a contamination problem. Halogen-containing nonionic polyglycol ether-type surface active agents have been described as useful for preparing germicidal-detergent compositions.

Numerous proposals have been made to provide biocidal compositions which involve the complexing of halogen, e.g., bromine and iodine, with various compounds which have the property of liberating the halogen under conditions of use. These compositions are generally referred to in the art as halophors, more particularly, iodophors and bromophors, and their disinfectant and germicidal activity is derived essentially from the free halogen which the compositions liberate.

Complexes of iodine with condensates of ethylene oxide and preformed poly(oxypropylene) glycol are disclosed in U.S. Pat. No. 2,759,869. Complexes of iodine monobromide with nonionic or anionic surface active agents are described in U.S. Pat. No. 2,868,686. Similarly, U.S. Pat. No. 4,131,556 describes forming a complex of iodine monobromide or the dibromine iodide ion, $[IBr_2]^-$, with nonionic surfactants such as fatty alcohols extended with ethylene oxide or alkylphenols extended with ethylene oxide. British Patent specifications Nos. 1,252,774 and 1,355,359 describe complexes of bromine with nonionic surfactants, such as alkyl aryl polyalkyleneoxy alkanol surfactants, polyalkyleneoxy alcohols, polyalkylene oxide block copolymers and polyalkyleneoxy esters of fatty acids.

The present invention provides halophor and halophor compositions comprising a complex of bromine and/or iodine, an organic carrier and halide, e.g., bromide, chloride or iodide ion. The halophor is easily handled, is water soluble and has exceptional stability. More particularly, the organic carrier is the dihalide of a poly(ethylene glycol). The molecular weight of the poly(ethylene glycol) dihalide may vary widely. For example, molecular weights up to about 5 million have been reported for the precursor poly(ethylene glycol).

In general, the poly(ethylene glycol) dihalide can be represented by the following graphic formula:

$$X(CH_2CH_2O)_nX \quad (I)$$

wherein X is halogen, i.e., chlorine, bromine or fluorine, and n is typically a number of at least 4. The average number of ethylene oxide units, i.e., "n", may vary widely, e.g., from about 4 to about 100,000, the latter corresponding to an average molecular weight of about 5 million (basis the poly(ethylene glycol) precursor). In a preferred embodiment, the poly(ethylene glycol) dihalide is a liquid. In a particular embodiment, n is a number of from about 4 to about 20, e.g., from about 8 to about 15. The halide is typically an alkali metal iodide or bromide, or alkaline earth metal chloride, bromide or iodide.

In accordance with another embodiment of the present invention, there is contemplated a halophor composition comprising a free-flowing, particulate, inert amorphous siliceous carrier having the halophor of the Present invention admixed therewith.

The halophor and halophor compositions described herein may be utilized as a source of halogen (bromine or iodine), e.g., as a halogenating agent. More particularly, they may be utilized for biocidal, e.g., sanitizing and disinfecting, applications. In those applications, the halophor is commonly added to the aqueous medium used to cleanse the surfaces to be cleaned, e.g., hospital floors, and food processing and handling equipment, whereby the halophor releases halogen, e.g., bromine, which forms hypohalite ion, e.g., hypobromite ion, in the aqueous medium, which hypohalite serves as the biocidal agent.

DETAILED DESCRIPTION OF THE INVENTION

Poly(ethylene glycol) dihalides that may be used as the organic carrier for halogen, e.g., bromine, are those represented by graphic formula I. By "organic carrier" is meant a poly(ethylene glycol) dihalide corresponding to graphic formula I that has the capacity to complex with elemental bromine and/or iodine and to carry the aforesaid complexed halogen into aqueous solution without precipitation or crystallization.

The organic carrier represented by graphic formula I may be prepared by converting the corresponding poly(ethylene glycol) precursor to its corresponding dihalide, e.g., the dichloride, $Cl(CH_2CH_2O)_nCl$. Poly(ethylene glycols) are well-known commercial compounds. A series of these water-soluble polymers having molecular weights up to several million are offered by the Union Carbide Company under the POLYOX ® trademark. The poly(ethylene glycol) resins may be represented by the graphic formula, $HO(CH_2CH_2O)_nH$, wherein n is typically at least 4, i.e., an average molecular weight of about 200. The average molecular weight of the resin can vary widely and a broad molecular weight range of such resins is available commercially. For example, POLYOX resins wherein n is a number from about 2000 to 100,000 (corresponding to molecular weights of from about 100,000 to 5 million) have been advertised. The average number of ethylene oxide units in the resin may, therefore vary from, for example, 4 to 100,000—corresponding to average molecular weights between 200 and 5 million. Resins in which the average number of ethylene oxide units vary from about 4 to about 450, e.g., about 4 to about 150, more particularly, 4 to 100 or 4 to 50, are contemplated for use in the preparation of the dihalides used to form the halophor complex described herein. Also contemplated particularly are resins wherein the average number of ethylene oxide units range from about 450 to 2000.

In particular, those polymers having a molecular weight of less than 700, and which are liquid at room temperature (23° C.), are deemed particularly useful for ease in processing. More particularly, such polymers may have average molecular weights of about 200, 300, 400 or 600. Resins having average molecular weights of from 1000 to 20,000 are white waxy solids at room temperature. These resins have liquidus temperatures ranging from about 35° C. to about 65° C. Resins with average molecular weight of 1000, 1540, 2000, 4000, 6000, 9000 and 20,000 have been described, i.e., resins wherein the average number of ethylene oxide units range from about 20 to about 450. Poly(ethylene glycol) resins that are not liquid at room temperature, may be dissolved in a suitable inert organic solvent (as described herein) for conversion to the corresponding dihalide with subsequent removal of the solvent.

The precursor polymers may be prepared by polymerizing ethylene glycol in the presence of Lewis acids or Lewis bases, e.g., sodium hydroxide. The polymerization is generally carried out under pressure, usually 20 to 50 pounds per square inch (137kPa–344kPa), in order to shorten the reaction time. Polymerization temperatures employed are in the range of from about 120° C.–200° C. when basic catalysts are used or from about 50° C.–70° C. when Lewis acids are used. The molecular weight may be controlled by the choice of catalyst and catalyst concentration.

The designation of the number of alkyleneoxy units present per mole of the aforedescribed polymer molecule, i.e., the letter "n", designates the average number of moles of alkylene oxide present per mole of organic polymer, i.e., the poly(ethylene glycol) or poly(ethylene glycol) dihalide, and hence the value of "n" in graphic formula I or the formula for the poly(ethylene glycol) resins may be a fractional number. Even though "n" is denoted as an integer, each polymeric molecule contains a distribution of units with the "n" value representing the average number of moles of alkylene oxide per mole of polymer.

Conversion of the poly(ethylene glycol) polymer to the corresponding dichloride or dibromide may be readily accomplished by reaction of the polymer with thionyl chloride or phosphorus trichloride, or phosphorous tribromide respectively by means well known in the art. Additionally, the polymer can be converted to the corresponding bis chloroformate, bisbromoformate or bisfluoroformate by reaction with phosgene, bromophosgene (carbonyl bromide) or carbonyl difluoride respectively. The resulting bischloroformate, bisbromoformate or bisfluoroformate may be converted to the corresponding dichloride, dibromide or difluoride by heating it in the presence of a catalytic amount of solid poly(vinyl pyridine), e.g., poly(4-vinyl pyridine), catalyst at between about 100° C. and 175° C. for from about 0.5 to about 10 hours. A suitable poly(vinyl pyridine) catalyst is a cross-linked poly(4-vinyl pyridine) available commercially from Reilly Tar and Chemical Corporation. Usually, from about 1 to 20 weight percent of the poly(vinyl pyridine) catalyst, basis the haloformate, is used. Preferably, the catalyst is substantially free of water, thereby avoiding the formation of hydrogen halide, e.g., hydrogen chloride, vapors during conversion of the haloformate to the dihalide.

In accordance with a preferred embodiment of the present invention, the added halide, e.g., alkali or alkaline earth metal halide, is first admixed with, or preferably dissolved (at least partially) in, the poly(ethylene glycol) dihalide (PEG dihalide) and subsequently halogen, i.e., bromine and/or iodine, introduced into the admixture or solution. While not wishing to be bound by any theory, it is believed that the halogen added to the PEG dihalide—added halide mixture reacts predominantly with the added halide to form polyhalo species rather than reacting irreversibly with the PEG dihalide, thereby providing a product which yields significant quantities of available halogen, e.g., bromine, for those applications requiring same. In a preferred embodiment, the PEG dihalide and added halide, e.g., lithium or sodium bromide, are substantially free of water, i.e., contains not more than about 5 weight percent water. Most preferably, the system is substantially anhydrous, which it is believed leads to enhanced stability of the halophor prepared in accordance with the present process.

The added halide, e.g., bromide, iodide or chloride used in the preparation of the halophor contemplated herein is provided usually by the bromides or iodides of the alkali metals, sodium, lithium or potassium, and the bromides, iodides or chlorides of the alkaline earth metals calcium and magnesium. Preferably, the aforesaid alkali metal halide is soluble or at least partially soluble in the poly(ethylene glycol) dihalide. Alternatively, anhydrous hydrogen bromide or hydrogen iodide may be used. The halide may be represented by the formula, MX, wherein M is hydrogen, an alkali or alkaline earth metal, and X is iodine, chlorine or bromine, e.g., MBr, MI, or MCl.

The amount of added halide used with PEG dihalide to prepare the halophor can vary. In general, the mole ratio of added halide ion to elemental halogen in the halophor, e.g., bromide:bromine ($Br_2$), may vary from 1:1 to 1:12, more usually from 1:1 to 1:3. Preferably, the mole ratio is about 1:2. Depending on the halide (bromide, chloride or iodide) ion and halogen (bromine or iodine) used, the halophor (bromophor or iodophor) may contain one or more of the following halide or interhalide species: $Br_3^-$ and $Br_2$ multiples thereof, e.g., $Br_5^-$, $Br_7^-$, $Br_9^-$ etc; $Br_2I^-$ and $Br_2$ multiples thereof, e.g., $Br_4I^-$, $Br_6I^-$; $BrI_2^-$ and $Br_2$ or $I_2$ multiples thereof, e.g., $Br_3I_2^-$, $Br_5I_2^-$, $BrI_4^-$, and $BrI_6^-$ etc; and $I_3^-$ and $I_2$ multiples of $I_3^-$, e.g., $I_5^-$, $I_7^-$, etc.; $Br_2Cl^-$ and $Br_2$ multiples thereof; and $I_2Cl^-$ and $I_2$ multiples thereof.

The amount of halogen, e.g., bromine, complexed with the PEG dihalide-added halide mixture may vary widely. Usually the amount of halogen present in the halophor as available elemental halogen, e.g., $Br_2$ or $I_2$, will vary from about 10 to about 50, e.g., 25 to 40, weight percent.

Halophors described herein can be readily produced by combining the PEG dihalide, added halide, e.g., alkali metal halide, and bromine (and/or iodine) under suitable complexing conditions. For bromophors, it is preferred that liquid bromine be combined with a mixture, e.g., solution, of liquid PEG dihalide and alkali or alkaline earth metal bromide, e.g., sodium, calcium or lithium bromide. The reaction between liquid bromine and the PEG dihalide - added halide liquid mixture is generally highly exothermic and hence the reaction mixture should be vigorously stirred and cooled if necessary as the bromine is added slowly. It is generally advisable to maintain the temperature of the reaction mixture from about 25° C. to about 55° C., more usually between 40° C. and about 50° C., for best results. The reaction between iodine and the PEG dihalide - added halide liquid mixture is generally less exothermic than when bromine is used; however, the same precautions and temperatures may be used to prepare the iodophors as are used to prepare the bromophors. Temporary temperature excursions outside the aforedescribed range will yield satisfactory results as long as temperatures at which the halogen reacts irreversibly with the PEG dihalide are avoided for extended periods of time. As described, the halophor is preferably prepared in the substantial absence of water, i.e., either added water or water present in the reactants, to achieve enhanced stability of the halophor. Small amounts of water, e.g., from 1 to 5 weight percent, basis the halophor complex, may be tolerated.

Poly(ethylene glycol) dihalides that are not liquids at or near room temperature, e.g., from about 18° C. to about 45° C., may be dissolved in a suitable organic solvent, such as methanol, and the halophor prepared in solution. Subsequently, the solvent is removed from the halophor. Organic solvents that may be used are those which are relatively inert, i.e., do not react chemically with the dihalide or halogen used to prepare the halophor, capable of dispersing and preferably dissolving the metal halide, and which may be readily separated from the halophor, e.g., by distillation. Dihalides that have liquidus temperatures in the 25°–45° C. range may be heated to convert them to the liquid state for conversion to the halophor.

Stabilizers, such as acids that are stable under the conditions of use, may be added to the halophor. Some acids that have been suggested for use as stabilizers for halophors, e.g., bromophors, are hydrochloric acid, hydrobromic acid, phosphoric acid, and acetic acid.

The halophors of the present invention may be adsorbed onto or admixed with a siliceous carrier to provide a halophor composition that may be used to provide a biocidal amount of the halophor or as a source of halogen, e.g., bromine, i.e., as a halogenating (brominating) agent.

The siliceous carrier is an inert particulate amorphous siliceous material which is free-flowing and water-insoluble, i.e., has a water solubility at 20° C. of less than 0.5 grams per liter. The siliceous material is chemically inert with respect to the halophor admixed therewith, e.g., the siliceous carrier does not react chemically with the halophor.

The particulate siliceous carrier is of such size as is suitable for the intended use of the herein described halophor, e.g., as a biocidal or brominating agent. The particles, for practical purposes, are generally in the range of from 10 to 400 mesh (U.S. Standard Screen), i.e., in the size range of between −10 and +400 mesh, usually −12 or −14, +325 mesh. The siliceous carrier will typically have an oil absorption of between about 75 and 350 milliliters of dibutyl phthalate per 100 grams of silica. Oil absorption values can be obtained using a method like that described in ASTM D2414-65. For most applications, the oil absorption of the siliceous carrier will be between about 150 and 300 milliliters/100 grams.

The siliceous carrier can be a synthetic amorphous silica or naturally occurring silica- or silicate-containing minerals. Examples of synthetic amorphous silicas that may be used as the carrier are precipitated silicas, fumed silicas and silica gels, including hydrogels and xerogels. The aforesaid subcategories of synthetic amorphous silicas refer generally to the method of their preparation. Precipitated silicas are prepared by mixing an alkali metal silicate, e.g., sodium silicate, and a mineral acid, e.g., hydrochloric acid, sulfuric acid or carbonic acid, to cause precipitation of very fine silica particles which are washed free of residual alkali metal salts and dried. Precipitated silicas may be prepared by the methods described in U.S. Pat. No. 2,940,830. Fumed silicas are generally prepared by the flame-hydrolysis of silicon tetrachloride to form a fine silica and by-product hydrochloric acid. Silica gel may be prepared by mixing an alkali metal silicate, e.g., sodium silicate, with a mineral acid at a pH and silica concentration such that a gelatinous precipitate (hydrogel) is formed. The hydrogel can then be washed to remove electrolytes either before or after drying, e.g., spray drying. When the hydrogel is dehydrated, a xerogel is formed. This may be accomplished by replacing the hydrogel water prior to the drying step with a readily volatile material, e.g., an alcohol.

Precipitated silica particularly useful as a carrier for the halophor described herein is material having a BET surface area of between about 130 and about 180 square meters per gram, an oil absorption of between 200 and 270, e.g., between about 230 and 260, milliliters of dibutyl phthalate per 100 grams of silica, a water absorption of between about 160 and 180 milliliters per 100 grams of silica, a median agglomerate particle size of between about 6 and 15, preferably between 8 and 12, microns (micrometers), as measured by a Coulter counter, and a specific volume of at least 3.5 cubic centimeters per gram, e.g., 3.5–4.7 $cm^3/g$, when compacted with an applied pressure of 17 pounds per square inch (psi) (117 kPa).

Such particularly useful precipitated silica may be prepared by (a) establishing an alkali metal silicate, e.g., sodium silicate, aqueous solution having an alkali metal oxide concentration of from about 5.6 to 7.2 grams per liter and a temperature of between about 190° F. (88° C.) and 198° F. (92° C.), (b) slowly adding from 2 to 5 times the original amount of alkali metal silicate to the aqueous solution while simultaneously acidifying the aqueous solution at a rate to maintain the alkali metal oxide concentration therein substantially constant, (c) adding further acidifying agent to the resulting slurry until the pH is from 8 to 9, (d) ageing the slurry at between 188° F. (87° C.) and about 198° F. (92° C.) for from 15 to 90 minutes, (e) adding additional acidifying agent to the aged slurry until the pH is from 4.0 to 4.7 and (f) separating (from the slurry), washing and drying the silica product.

Also contemplated for use as the siliceous carrier are naturally occuring silica- or silicate-containing minerals. These materials are rich in hydrated silicates of aluminum or magnesium and include such clays as montmorillonite, attapulgite, kaolinite, talc, bentonite, and Fuller's earth, diatomaceous earth, naturally occurring amorphous aluminum silicate (zeolites) and the synthetic zeolites which are an amorphous combination of precipitated alumina and silica. Also contemplated for use as a carrier herein are precipitated calcium silicates, which include synthetic silicas containing small amounts, e.g., 1 to 10 percent, of calcium, calculated as calcium oxide. The above-described synthetic siliceous materials are generally commercially available or can be prepared by techniques known in the art.

Particulate halophor compositions can be readily produced by admixing at least one siliceous carrier with the halophor, e.g., liquid bromophor, under conditions designed to obtain a homogeneous mixture. Liquid halophors can be applied to the particulate siliceous carrier by spraying, preferably while the siliceous carrier is stirred or tumbled, to achieve uniform distribution of the halophor on the carrier. Alternatively, the liquid halophor can be poured onto the granular carrier and the mixture thereafter stirred. Halophors that are relatively viscous can be heated slightly to place them in a free-flowing liquid form for making the particulate halophor composition. Generally, it is preferred to maintain the halophor at temperatures of 55° C. or less to prevent irreversible reaction of the halogen, e.g., bromine, with the PEG dihalide.

The amount of the bromophors or iodophors of the present invention admixed with the siliceous carrier may vary widely and may be up to that amount which causes the carrier to lose its free-flowing property, i.e., up to the maximum adsorptivity of the siliceous carrier utilized. The maximum amount of halophor that can be sorbed by the siliceous carrier usually is a function of the adsorbtivity of the carrier. A measure of a siliceous carrier's adsorbtivity is its oil absorption. The higher the oil absorption value for a particular siliceous carrier—the greater is the amount of halophor that can be retained by the carrier and still remain free-flowing.

The amount of bromophor or iodophor mixed with or sorbed onto the siliceous carrier is advisedly selected to provide a free-flowing, granular halophor composition containing at least a biocidal amount of available bromine and/or iodine (or bromiodide). Since the amount of iodine or bromine required for biocidal activity will vary with the end use, e.g., brominating agent, sanitizer or disinfectant, the quantity of halophor sorbed onto the carrier may likewise vary and will also depend on the amount of halogen, i.e., bromine and/or iodine, present in the bromophor that is available for the particular biocidal application.

It is contemplated that the siliceous carrier, depending on its adsorbtivity, may contain from about 1 to about 80 weight percent of the halophor, basis the weight of the siliceous carrier, e.g., between about 5 and 75 or 10 and 40, weight percent of halophor. For some applications between about 1 and 35 parts by weight of halophor per 100 parts by weight of the siliceous carrier may be sufficient.

It is contemplated that more than one amorphous siliceous carrier may be used to prepare the particulate halophor compositions of the present invention. Thus, mixtures of siliceous carriers may be used. It is further contemplated that particulate halophor compositions containing high levels of halophor (in the form of a masterbatch) may be prepared with highly absorptive siliceous carrier(s) and subsequently diluted with other chemically inert solid diluents, e.g., less adsorptive (and perhaps less costly) siliceous carriers, clays, and inorganic, preferably water soluble, salts. Such particulate halophor masterbatch compositions may contain from about 30 to about 80, e.g., 50 to 75, weight percent halophor. Inorganic salts contemplated are alkali metal sulfates, phosphates (orthophosphates and polyphosphates), carbonates and chlorides. The aforesaid salts of sodium and potassium are preferred for most applications. Preferably the inorganic salts are used in their anhydrous form.

The compositions of the present invention are more particularly described in the following examples which are intended as illustrative only since numerous modifications and variations therein will be apparent to those skilled in the art.

While the present invention has been illustrated by the preparation of bromophor compositions using a particular PEG dichloride, similar results are expected using bromophors prepared with other of the described PEG dihalides.

EXAMPLE I

Preparation of the Dichloride of Poly(ethylene glycol)

A pool of about 550 milliliters (713 grams–7.20 moles) of liquid phosgene having a temperature of 0° C. was established in a reaction flask. Three moles (1200 grams) of a poly(ethylene glycol) of about 400 molecular weight was added slowly to the phosgene pool over a period of 17–18 hours while maintaining the temperature of the reaction flask contents at 0° C. Excess phosgene was removed from the reaction flask by degassing slowly with nitrogen at room temperature for about 4 days. Thereafter, the reaction mixture was degassed with nitrogen at 50° C. for $2\frac{1}{2}$ hours. The acidity (as HCl) of the degassed polyethylene glycol bis chloroformate was found to be 0.21%.

Three hundred grams of the resulting bischloroformate was mixed with 30 grams of granular cross-linked poly(4-vinylpyridine) catalyst and the suspension heated for 5 hours at 130°–140° C. The resulting suspension of polyethylene glycol dichloride was filtered and 200 grams of a dark brown liquid recovered. The product assay was found to be 91%.

EXAMPLE II

A reaction flask was charged with 84.0 grams of the polyethylene glycol dichloride (PEGDC) of Example I. The PEGDC was heated to 45° C. and 16.0 grams (0.18 mole) of lithium bromide dissolved therein. Following addition of the lithium bromide, 61.3 grams (0.38 mole) (19.8 milliliters) of bromine ($Br_2$) were added slowly with stirring over forty five minutes to the reaction flask. After all of the bromine had been added, the reaction mixture was stirred an additional ten minutes, allowed to cool to 30° C., and stored in a glass bottle at 30° C. for 16 weeks after which the test was terminated. Periodically a sample was removed from the glass bottle and tested by thiosulfate titration for the amount of available bromine remaining in the stored composition. Results are tabulated in Table I. The bromophor composition comprised 52.1 weight percent of PEGDC, 9.9 weight percent lithium bromide and 38.0 weight percent of added bromine.

TABLE I

| Time, Wks. | % Available Bromine | Time, Wks. | % Available Bromine | Time, Wks. | % Available Bromine |
|---|---|---|---|---|---|
| Start | 32.1 | 5 | 31.0 | 11 | 31.5 |
| 3 Days | 32.0 | 6 | 30.5 | 12 | 30.4 |
| 1 | 31.8 | 7 | 32.4 | 13 | 31.1 |
| 2 | 32.0 | 8 | 31.8 | 14 | 30.4 |
| 3 | 32.0 | 9 | 31.4 | 15 | 30.0 |
| 4 | 32.0 | 10 | 31.7 | 16 | 31.5 |

The data of Table I show that the bromophor composition of Example II remained relatively stable over 16 weeks—the amount of available bromine at that time being substantially the same as the amount of bromine available when the composition was made.

Example III (Comparative)

A reaction flask was charged with 100 grams of the PEGDC of Example I. Bromine in the amount of 61.3 grams (0.38 mole) (19.8 milliliters) ($Br_2$) was added with stirring over 5 minutes to the flask. The temperature of the contents in the reaction flask rose from room temperature to 38° C. Thereafter, the temperature increased to 45° C. and the flask placed in an ice bath until the temperature decreased to 38° C. After being removed from the ice bath, the temperature rose briefly to 42° C. The reaction flask was allowed to cool to 30° C. and the sample stored at 30° C. in a glass bottle for 7 weeks after which the test was terminated. The bromine added to the bromophor represented 38.0 weight percent of the composition. Of that amount 25.7 weight percent was retained in an available form initially. Periodically, a sample of the bromophor was removed from the glass bottle and tested by thiosulfate titration for the amount of available bromine remaining in the stored composition. Results are tabulated in Table II.

TABLE II

| Time, Wks. | % Available Bromine | Time, Wks. | % Available Bromine |
|---|---|---|---|
| Start | 25.7 | 4 | 8.7 |
| 3 Days | 17.6 | 5 | 8.4 |
| 1 | 15.4 | 6 | 7.6 |
| 2 | 12.4 | 7 | 7.3 |
| 3 | 10.6 | Test Terminated. | |

Although the present invention has been described with reference to specific details of certain embodiments thereof, it is not intended that such details should be regarded as limitations upon the scope of the invention except as and to the extent that they are included in the accompanying claims.

We claim:

1. A halophor comprising a complex of (a) elemental halogen selected from the group consisting of bromine and iodine, (b) dihalide of poly(ethylene glycol), and (c) added halide represented by the formula MX, wherein M is hydrogen, alkali metal or alkaline earth metal, and X is bromine, chlorine or iodine, the mole ratio of added halide to halogen being from about 1:1 to 1:12, and the amount of elemental halogen in the halophor complex being between about 10 and about 50 weight percent.

2. The halophor of claim 1 wherein the poly(ethylene glycol) dihalide is represented by the graphic formula, $X(CH_2CH_2O)_nX$, wherein X is chlorine, bromine or fluorine and n is a number of from about 4 to 100,000.

3. The halophor of claim 2 wherein the poly(ethylene glycol)dihalide is normally liquid and n is a number from about 4 to about 20.

4. The halophor of claim 2 wherein n of the graphic formula for the poly(ethylene glycol) dihalide is from about 4 to about 450.

5. The halophor of claim 2 wherein n of the graphic formula for the poly(ethylene glycol) dihalide is from about 2000 to about 100,000.

6. The halophor of claim 3 wherein n is a number between about 8 and about 15.

7. The halophor of claim 2 wherein n is a number between about 450 and 2000.

8. The halophor of claim 1 wherein the mole ratio of added halide to halogen is from about 1:1 to 1:3 and the amount of elemental halogen in the halophor is from about 25 to 40 weight percent.

9. The halophor composition of claim 8 wherein the alkali metal halide is selected from the bromides and iodides of sodium, lithium, and potassium and the bromides, iodides and chlorides of calcium and magnesium.

10. A bromophor comprising a complex of (a) elemental bromine, (b) dichloride of poly(ethylene glycol), and (c) added bromide represehted by the formula MBr, wherein M is hydrogen, alkali metal or alkaline earth metal, the mole ratio of added bromide to bromine being from about 1:1 to 1:12, and the amount of elemental bromine in the bromophor being between about 10 and about 50 weight percent.

11. The bromophor of claim 10 wherein the mole ratio of added bromide to bromine is from about 1:1 to 1:3 and the amount of elemental bromine in the bromophor is from about 25 to 40 weight percent.

12. The bromophor of claim 10 wherein the alkali metal bromide is sodium bromide, lithium bromide, or potassium bromide.

13. The bromophor of claim 10 wherein the poly(ethylene glycol) dihalide is represented by the graphic formula $Cl(CH_2CH_2O)_nCl$ wherein n is a number of from about 4 to 100,000.

14. The bromophor of claim 13 wherein n is a number of from about 4 to about 20.

15. The bromophor of claim 13 wherein n is a number of from about 4 to about 450.

16. The bromophor of claim 13 wherein n is a number of from about 2000 to about 100,000.

17. The bromophor of claim 12 wherein n is a number of from about 4 to about 20.

18. A free-flowing particulate halophor composition comprising particulate, inert, amorphous siliceous carrier and from about 1 to about 80 weight percent of a complex of (a) halogen selected from the group consisting of bromine and iodine, (b) dihalide of poly(ethylene glycol) and (c) halide represented by the formula, MX, wherein M is hydrogen, alkali metal or alkaline earth metal and X is bromine or iodine, the mole ratio of halide to halogen being from about 1:1 to 1:12, and the amount of halogen in the complex being between about 10 and about 50 weight percent.

19. The halophor composition of claim 18 wherein the siliceous carrier is a synthetic amorphous silica or naturally occurring silica- or silicate-containing mineral.

20. The halophor composition of claim 19 wherein the siliceous carrier contains from about 5 to about 75 weight percent of the complex.

21. The halophor composition of claim 19 wherein the mole ratio of halide to halogen is from about 1:1 to 1:3 and the amount of halogen in the complex is from about 25 to 40 weight percent.

22. The halophor composition of claim 21 wherein the siliceous carrier is precipitated amorphous silica.

23. The halophor composition of claim 22 wherein the alkali metal halide is selected from the bromides and iodides of lithium, sodium, or potassium, and the alkaline earth metal halide is selected from the bromides, iodides and chlorides of calcium and magnesium.

24. The halophor composition of claim 19 wherein the halogen is bromine, the dihalide of poly(ethylene glycol) is the dichloride, and the halide is sodium bromide, lithium bromide, or potassium bromide.

25. The halophor composition of claim 24 wherein the poly(ethylene glycol) dichloride is represented by the graphic formula, $Cl(CH_2CH_2O)_nCl$, wherein n is a number of from 4 to 100,000.

26. The halophor composition of claim 25 wherein n is a number of from about 4 to about 450.

27. The halophor composition of claim 25 wherein n is a number of from about 4 to about 20.

28. The halophor composition of claim 27 wherein the siliceous carrier is precipitated amorphous silica.

29. A method for preparing a halophor comprising a complex of (a) elemental halogen selected from the group consisting of bromine and iodine, (b) dihalide of poly(ethylene glycol) and (c) added halide represented by the formula MX, wherein M is hydrogen, alkali metal, or alkaline earth metal, and X is bromine, chlorine or iodine, comprising admixing the dihalide and added halide, said added halide being at least partially soluble in the dihalide, and thereafter introducing halogen into the poly(ethylene glycol) dihalide—added halide mixture in amounts sufficient to provide between about 10 and about 50 weight percent halogen, basis the halophor complex, the mole ratio of added halide to halogen being from about 1:1 to 1:12.

30. The method of claim 29 wherein the added halide is dissolved in the poly(ethylene glycol) dihalide prior to introducing the halogen.

31. The method of claim 29 wherein the temperature at which the halophor complex is prepared is from about 25° C. to about 55° C.

32. The method of claim 31 wherein the halogen is bromine and the added halide is selected from the bromides and iodides of sodium, lithium and potassium, and the bromides, chlorides and iodides of calcium and magnesium.

33. The method of claim 31 wherein the halogen is bromine and the added halide is sodium bromide, lithium bromide or potassium bromide.

34. The method of claim 31 wherein the halophor is prepared in the substantial absence of water.

* * * * *